Figure 5:
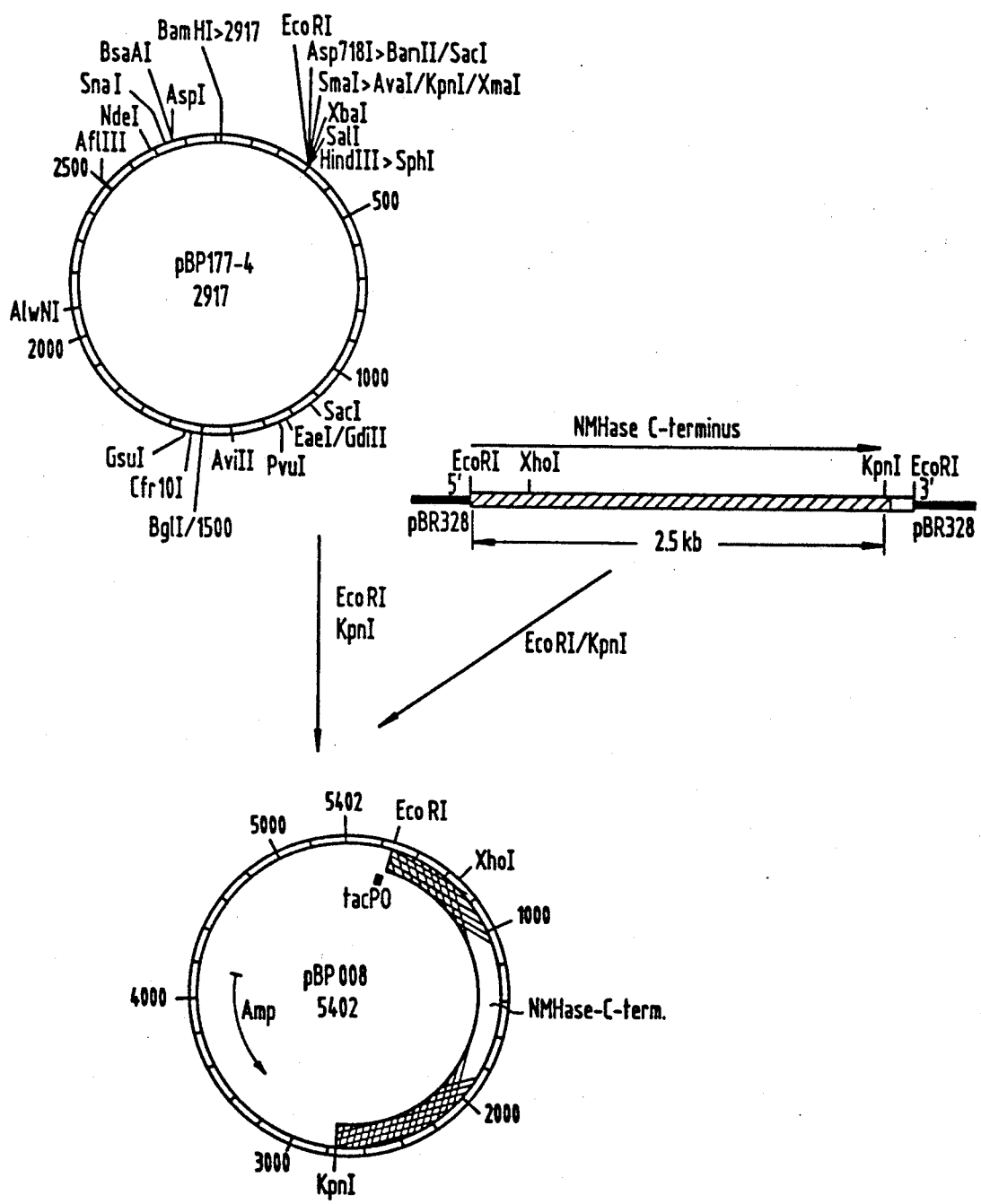

United States Patent [19]

Schumacher et al.

[11] Patent Number: 5,213,969
[45] Date of Patent: May 25, 1993

[54] CLONED N-METHYLHYDANTOINASE

[75] Inventors: Günther Schumacher, Bernried; Helmut Burtscher, Habach; Hans Möllering, Tutzing, all of Fed. Rep. of Germany

[73] Assignee: Boehringer Mannheim, GmbH, Mannheim-Waldhof, Fed. Rep. of Germany

[21] Appl. No.: 727,814

[22] Filed: Jul. 8, 1991

[30] Foreign Application Priority Data

Jul. 6, 1990 [DE] Fed. Rep. of Germany ....... 4021571

[51] Int. Cl.$^5$ .................... C12P 21/02; C12N 15/54; C12N 1/21
[52] U.S. Cl. ................. 435/69.1; 435/320.1; 435/252.3; 435/252.33; 435/240.1; 435/193; 536/23.2; 935/14
[58] Field of Search ............ 536/27; 435/320.1, 252.3, 435/252.33, 69.1, 195, 240.1

[56] References Cited

U.S. PATENT DOCUMENTS 4,816,393  3/1989  Siedel et al. ...................... 435/18

FOREIGN PATENT DOCUMENTS 0154269  4/1987  European Pat. Off. .
0219034  4/1987  European Pat. Off. .
0437254A2  7/1991  European Pat. Off. .

OTHER PUBLICATIONS

Berger et al. Guide to molecular Cloning Techniques. Methods in Enzymlogy 152 Academic Press. 1987.
Suggs, et al. Proc. Nat. Acad Sci. USA 78:6613–6617 (1981).
Young, et al Proc. Nat. Acad Sci. USA 80 1194–1198 (1983).
Biological Abstracts, vol. 86, No. 5, 1988 "Fully enzymatic colorimetric assay of serum and urine creatinine which obviates the need for sample blank measurements".
WO-A-8 809 373 (Boehringer Mannheim GmbH).

Primary Examiner—Robert A. Wax
Assistant Examiner—G. Bugaisky
Attorney, Agent, or Firm—Nikaido, Marmelstein, Murray & Oram

[57] ABSTRACT

The invention concerns a DNA which codes for a protein with N-methylhydantoinase activity and which has
(1) the nucleic acid sequence shown in FIG. (1),
(2) a sequence corresponding to it within the scope of the degeneracy of the genetic code or
(3) a sequence which hybridizes with a sequence from (1) or/and (2) under stringent conditions.

Furthermore the invention also concerns a recombinant vector which contains a DNA according to the present invention, a cell which is transformed with a vector according to the present invention as well as a process for producing a recombinant protein with NMHase activity.

22 Claims, 7 Drawing Sheets

Fig.1
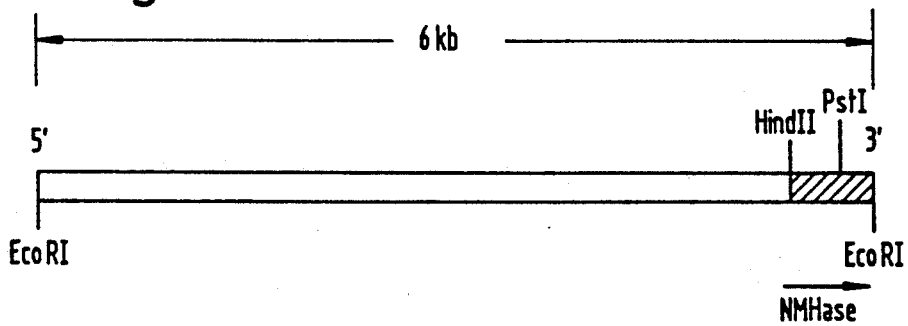
Fig.2
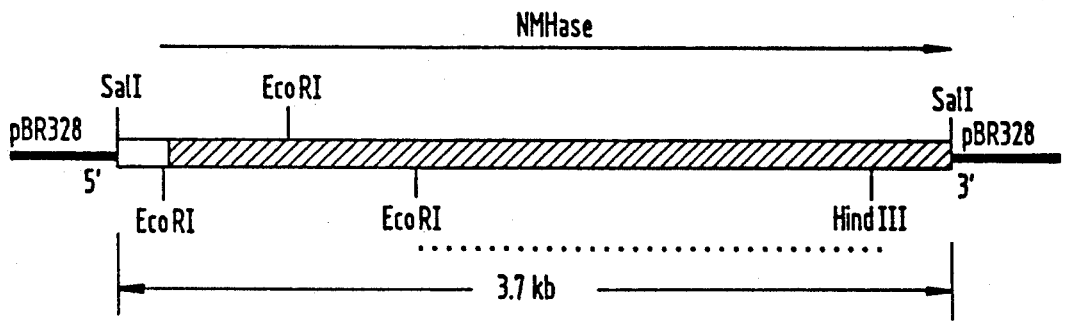
Fig.3
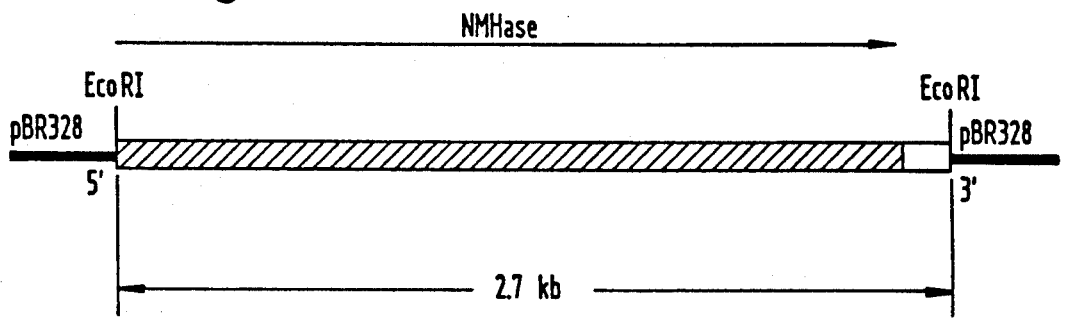
Fig.4
Linker Fragment
```
5'-AATTCTTATGAAGCGCATCGGAGTAGACGT-3'
   ||||||||||||||||||||||||||
3'-    GAATACTTCGCGTAGCCTCATC-5'
```

CLONED N-METHYLHYDANTOINASE

The enzyme N-methylhydantoinase (NMHase) is required for the determination of the content of creatinine in liquids. The creatinine level is an important parameter for kidney diagnostics. Annually about one thousand million tests are carried out worldwide. Therefore the provision of the enzyme NMHase at a low cost, as well as the possibility of an unproblematic fermentation are basic requirements for the provision of diagnostic kits for the determination of creatinine. The molecular weight of NMHase is 125 kD in an SDS gel. The specific activity is 2 U/mg, the for N-methylhydantoin is $2 \times 10^{-5}$ mol/l. NMHase is usually isolated from Arthrobacter. However, this process has drawbacks which are related to the microorganism used.

Improved methods of isolation must therefore be developed in order to provide larger amounts of NMHase. This was also the object of the present invention.

The object according to the present invention could be achieved by cloning the gene coding for the NMHase from Arthrobacter and expressing it in a suitable host organism.

The present invention thus provides a DNA which contains (1) the nucleic acid sequence shown in SEQ ID NO: 1, (2) a sequence corresponding to it within the scope of the degeneracy of the genetic code or (3) a sequence which hybridizes with the sequences from (1) or/and (2) under stringent hybridization conditions and which codes for a protein with NMHase activity.

In this connection reference is made to Maniatis et al. (1982) "Molecular Cloning. A laboratory manual", Cold Spring Harbor Laboratory, New York, for the meaning of hybridization under stringent conditions in the present invention.

The DNA according to the present invention codes for a protein with 1288 amino acids whose sequence is shown in SEQ ID NO: 2. The present invention thus also encompasses a protein with NMHase activity and with the amino acid sequence shown in SEQ ID NO: 2 or an amino acid sequence derived therefrom, which is obtained by genetic engineering methods e.g. by expression in a heterologous organism i.e. in an organism in which the gene coding for the protein according to the present invention does not originally occur. On the other hand, it is also possible to achieve an improved expression of the NMHase gene by introducing one or several copies of the DNA according to the present invention into an organism in which a DNA according to the present invention is present The present invention in addition provides a recombinant vector which contains one or several copies of a DNA according to the present invention. A recombinant vector according to the present invention can be a vector which is suitable for protein expression in prokaryotic or eukaryotic organisms. It is preferably a prokaryotic vector.

A recombinant vector according to the present invention can be a vector which is present extrachromosomally in a host cell (e.g. plasmid) or is integrated into the genome of the host (e.g. bacteriophage lambda). The recombinant vector according to the present invention is preferably a plasmid. A suitable plasmid according to the present invention is e.g. the plasmid pBP010.

The DNA which codes for a protein with NMHase activity is located on a recombinant vector according to the present invention and is preferably under the control of a regulatable promoter, which means that an expression of the DNA according to the present invention can be suppressed for example by a repressor and only takes place when the regulatable promoter is specifically induced. This induction can for example take place by a change in temperature or by addition of a chemical inducer (e.g. IPTG for lac promoter derivatives). In a particular preferred embodiment of the present invention the regulatable promoter which is intended to control the NMHase gene is the mgl promoter from Salmonella typhimurium (WO 88/09373) which can be regulated by means of catabolite repression by sugars such as e.g. glucose and fructose.

A suitable vector according to the present invention for the expression of NMHase in gram-negative bacteria, in particular *E. coli*, is e.g. the plasmid pBP006. In order to construct pBP006, a DNA fragment, which contains the sequence of the mgl promoter from Salmonella typhimurium, was isolated from the plasmid pPZ07-mgl-lac (described in WO 88/09373, FIG. 8) and cloned upstream of a DNA fragment which contains the sequence coding for the NMHase gene from Arthrobacter without its own promoter.

The present invention also provides a cell which is transformed with a DNA according to the present invention or with a recombinant vector according to the present invention. This cell is preferably a bacterial cell, particularly preferably an *E. coli* cell.

The DNA according to the present invention is obtained by cloning the NMHase gene. Chromosomal DNA from Arthrobacter was isolated for this by conventional methods and cleaved with suitable restriction enzymes. A gene bank of these DNA fragments was set up in *E. coli*. However, a cloning of the NMHase gene in the usual manner (screening the gene bank with oligonucleotide probes and selection of the clones by means of NMHase activity) did not succeed. In fact no NMHase activity was found in any of the Arthrobacter DNA fragments used when cloned in *E. coli*. This finding was surprising since a DNA fragment of the correct length with a start and stop codon could be identified on the basis of hybridization with the oligonucleotide probe. An NMHase activity could only be detected when cloning DNA fragments on which the native NMHase promoter was absent.

The invention also provides a process for the production of a protein with NMHase activity in which a cell is transformed with a DNA according to the present invention or with a recombinant vector according to the present invention, the transformed cells are cultured in a suitable medium and the protein is isolated from the medium or the cells.

*E. coli* bacteria are preferably used as the host organism for the process according to the present invention. In this connection it is, however, advantageous to culture the transformed cells under suboptimal growth conditions. Suboptimal growth conditions are for example understood as a reduced temperature during the incubation (30° C. or less), a reduction of the oxygen transfer or/and the use of a minimal medium (i.e. a medium which contains certain essential nutrients for the cultured organism in limiting concentrations).

Thus for instance the culture conditions in a process for the isolation of NMHase from *E. coli*, in which a recombinant vector is used which contains the NMHase gene under the control of the tac promoter, is a minimal medium, an incubation temperature of less than 30° C. and an incomplete induction of the tac promoter with 0.8% lactose.

The particularly preferred expression of the NMHase gene under the control of the mgl promoter of Salmonella typhimurium preferably also takes place at an incubation temperature of 30° C. or less, which if desired is coupled with an additional reduction of the oxygen transfer so that the NMHase formed does not accumulate in an inactive form as precipitation bodies. The mgl promoter is regulated by catabolite repression (U.S. patent application Ser. No. 300,357).

In general it is preferred for the process according to the present invention that the induction of the regulatable promoter used in each case is only carried out incompletely which also contributes to a reduced formation of precipitation bodies.

In addition it is particularly preferred for the process according to the present invention that, for the purpose of stabilization and preferably during the isolation of the NMHase from the transformed cells or the medium, the protein is incubated with the enzyme substrate N-methylhydantoin. Surprisingly the stability of the recombinant NMHase obtained by the process according to the present invention can be substantially increased by the presence of an amount of approximately 3.8 nmol N-methylhydantoin per unit (U) of the enzyme. For this the enzyme is incubated with a N-methylhydantoin solution, preferably at a concentration of 1 to 100 mmol/l, particularly preferably of 10 to 70 mmol/l, most preferably of 50 mmol/l. In this incubation step it is advantageous to increase the temperature to e.g. 55° C. It is especially surprising that the presence of its own substrate stabilizes the enzyme and that at the same time the enzymatic reaction of the recombinant enzyme does not interfere.

The present invention also encompasses a reagent for the determination of the content of creatinine in liquids which contains a protein obtained according to a process according to the present invention in addition to the usual constituents.

The following examples are intended to further elucidate the invention in conjunction with the sequence protocols and FIGS. 1 to 10.

Figure 6:
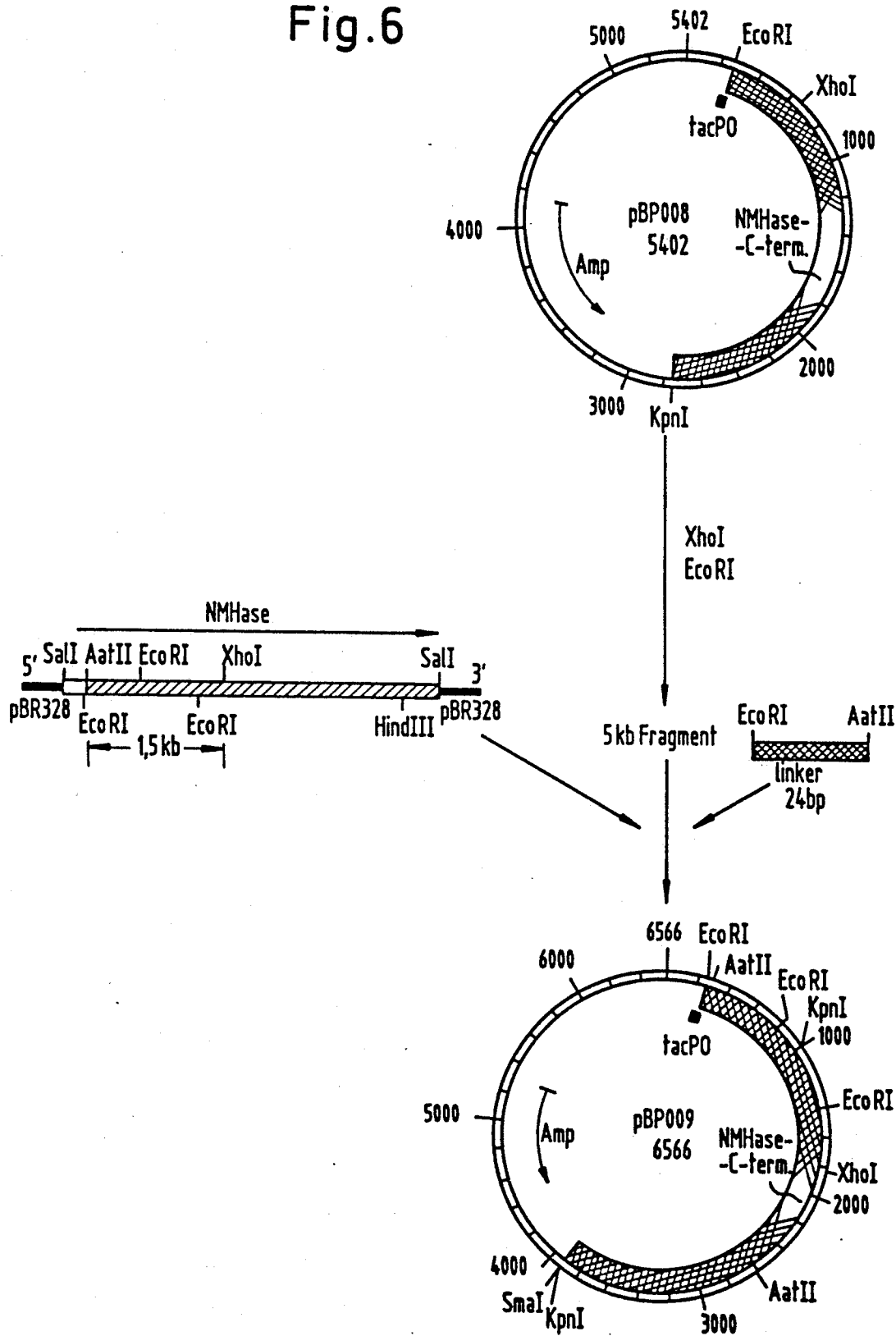
Figure 7:
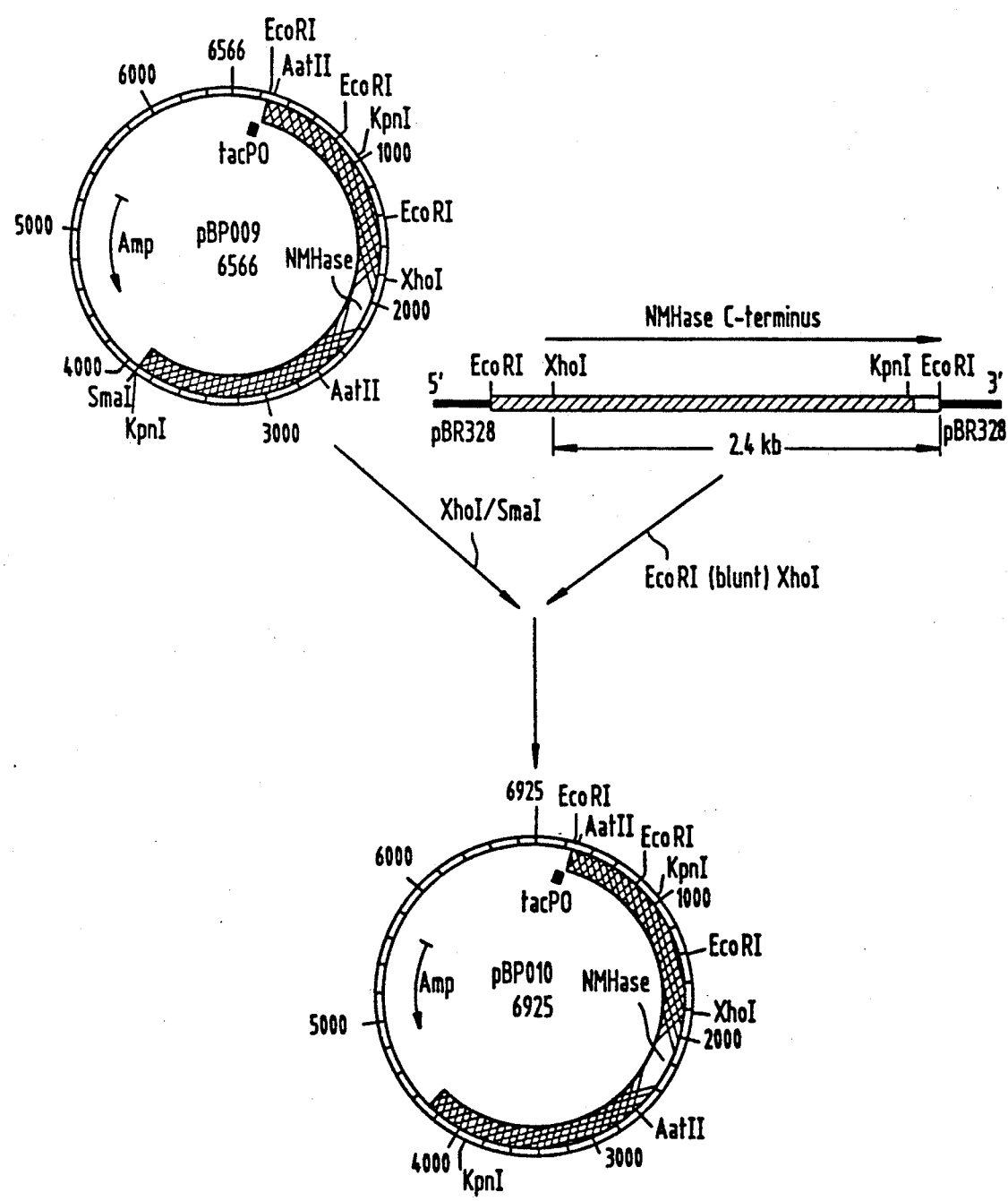
Figure 8:
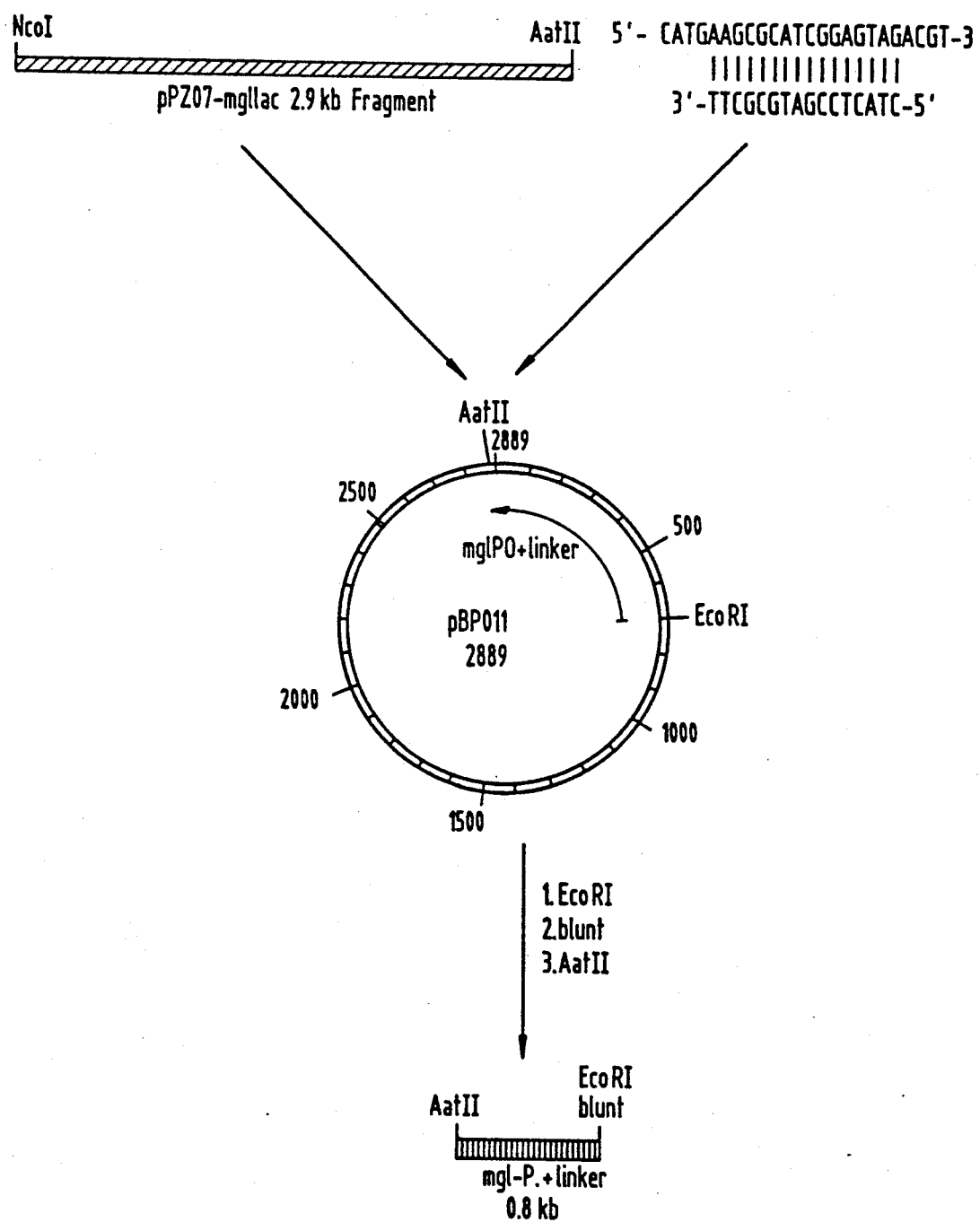
Figure 9:
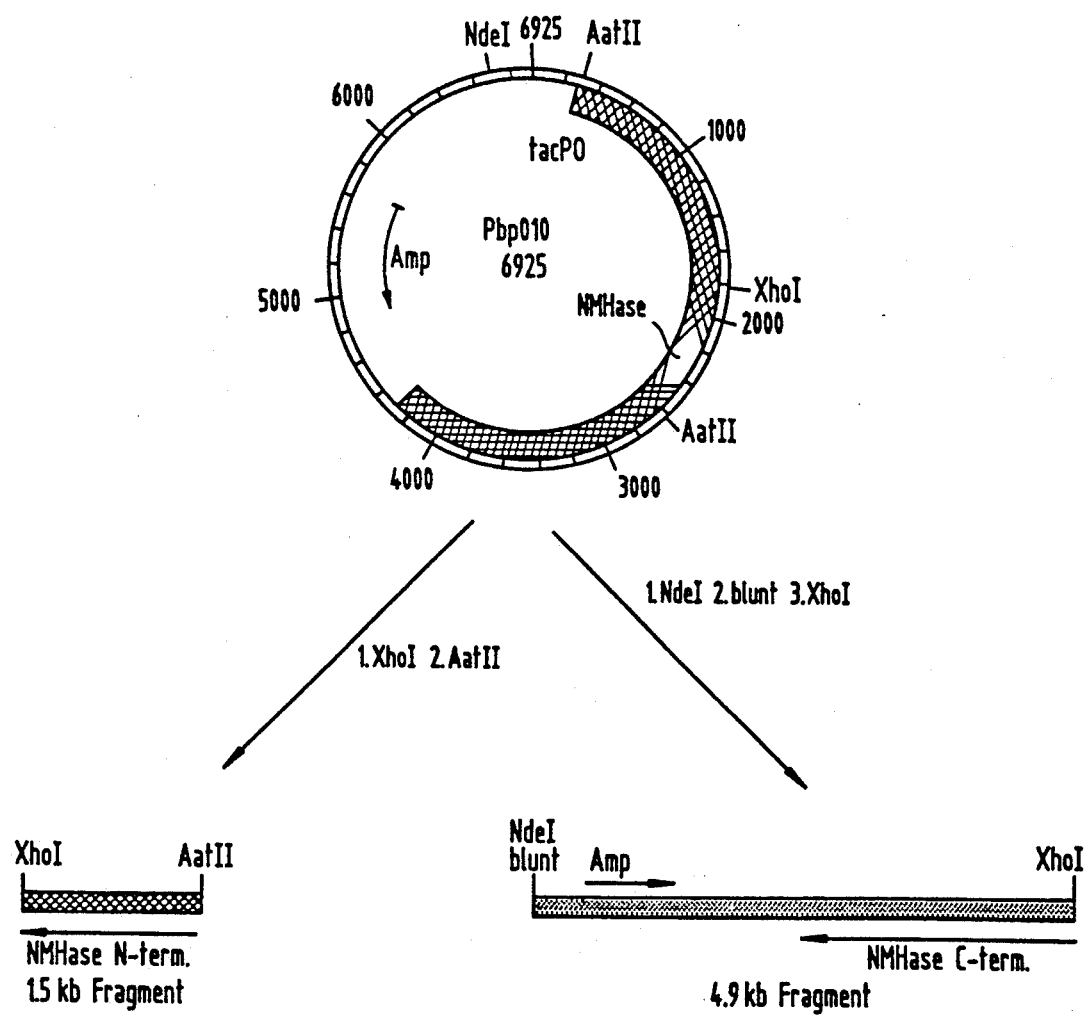
Figure 10:
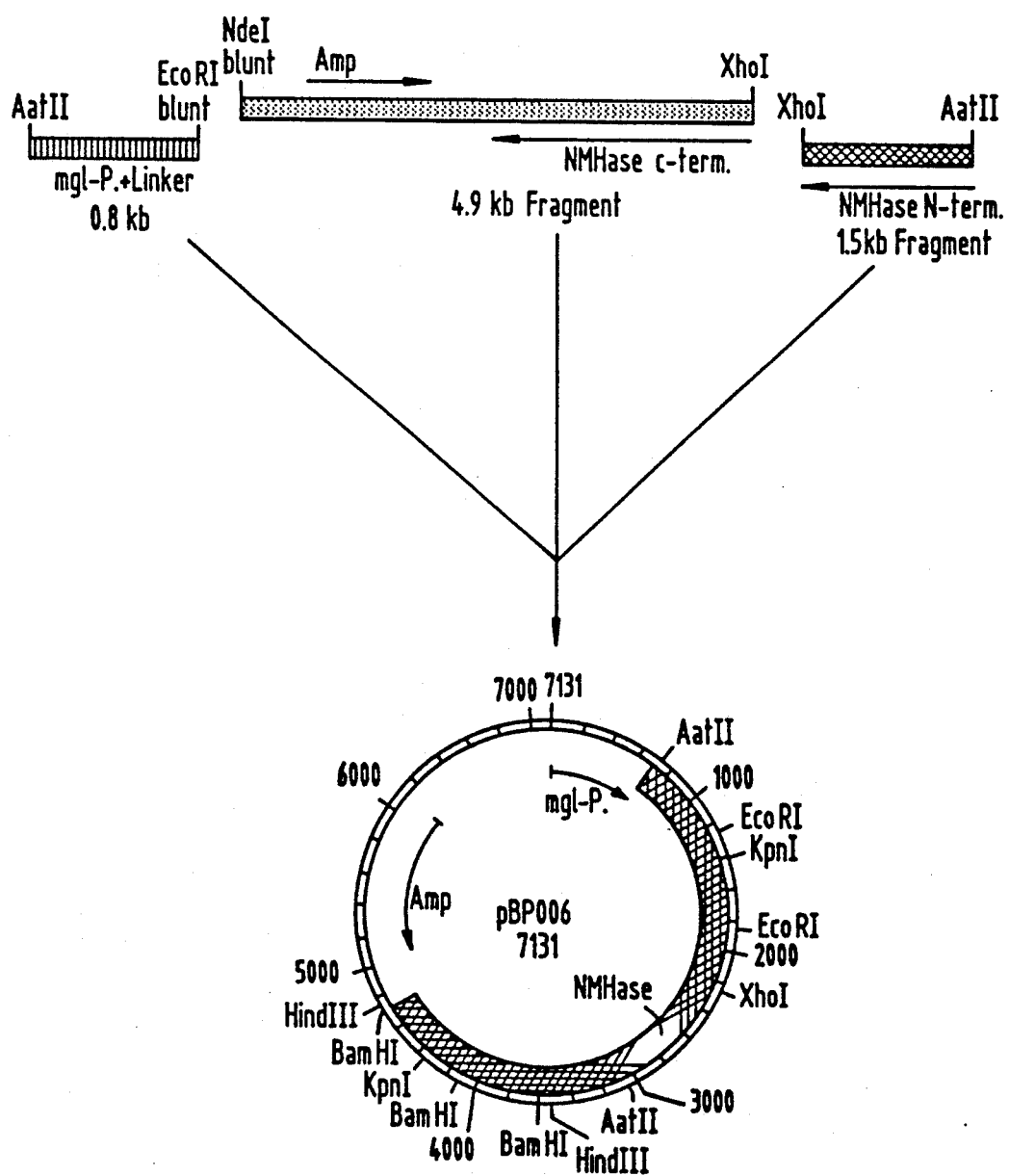

SEQ ID NO: 1 shows the DNA sequence of the NMHase gene,

SEQ ID NO: 2 shows the amino acid sequence of the NMHase derived therefrom,

FIG. 1 shows a 6 kb long EcoRI fragment from Arthrobacter with a ca. 0.6 kb long fragment of the NMHase gene, FIG. 2 shows a 3.7 kb long SalI fragment from Arthrobacter with a 3.0 kb long region coding for the NMHase gene, FIG. 3 shows the 3'-terminal region of the NMHase gene, FIG. 4 shows an EcoRI/AatII linker, FIG. 5 shows the construction of the plasmid pBP008, FIG. 6 shows the construction of the plasmid pBP009, FIG. 7 shows the construction of the NMHase expression plasmid pBP010, FIG. 8 shows the construction of the plasmid pBP011 with the mgl promoter from Salmonella typhimurium, FIG. 9 shows the isolation of fragments of the NMHase gene from pBP010, FIG. 10 shows the construction of the NMHase expression plasmid pBP006.

EXAMPLE 1

Cloning of the NMHase

DNA was isolated according to the usual methods from Arthrobacter spec. DSM 2563 (J. Marmur—A procedure for the isolation of deoxyribonucleic acid from microorganisms, J.Mol.Biol. 3, 208–218 (1961); S. VisuVanathan et al.—Simple enzymic method for isolation of DNA from diverse bacteria, Journal of Microbiological Methods 10, 59–64 (1989)) and cleaved with the restriction enzymes EcoRI or HindIII. Bacteriophage λgt10 (Boehringer Mannheim GmbH) was used as the cloning vector for the Arthrobacter DNA. The Arthrobacter DNA was cloned in λgt10 according to the instructions of the producer.

The Arthrobacter gene bank obtained was screened with an oligonucleotide probe which was derived from a partial peptide sequence of NMHase.

Partial peptide sequence of NMHase: (SEQ ID NO: 3) Met Lys Arg Ile Gly Val Asp Val Gly Gly Thr Phe Thr Asp Leu Tyr Phe.

The following oligonucleotide probes were derived from this partial peptide sequence 1. ATG AA(G/A) (C/A)G(G/A) AT(A/C/T) GG(G/A/T/C) GT (SEQ ID NO: 4)
2. ATG AA(G/A) (C/A)G(T/C) AT(A/C/T) GG(G/A/T/C) GT (SEQ ID NO: 5)
3. ATG AAG CGC ATC GGC GTG GAC GTG GGC GGC ACG TTC ACC (SEQ ID NO: 6) GAT CTG TAC TT Using these oligonucleotide probes a 6 kb long EcoRI fragment was found in the λLgt10 gene bank which contains a part of the NMHase gene (ca. 0.6 kb) (FIG. 1).

A part of this fragment (ca. 300 bp between the cleavage sites PstI and EcoRI) was radioactively labelled with $^{32}P$. Subsequently Arthrobacter DNA was cleaved with the restriction enzyme SalI, separated on an agarose gel and hybridized in a Southern Blot with the radioactively labelled DNA fragment. The hybridizing DNA region was cut out of the agarose gel and cloned into the SalI restriction cleavage site of the tetracycline resistance gene of pBR328 (Boehringer Mannheim GmbH).

An examination of E. coli cells transformed with this plasmid resulted in a 3.7 kb long DNA fragment which contains a 3.0 kb long region of the NMHase gene (FIG. 2).

The EcoRI/Hind III fragment from this insertion which is marked by a dotted line was labelled with digoxigenin (Boehringer Mannheim, Dig Kit). The λgt10 gene bank already mentioned above was again screened with this probe whereby a 2.7 kb piece was found which contains the 3'-terminal region of the NMHase gene (FIG. 1). This DNA fragment was also cloned into the vector pBR328.

EXAMPLE 2

Expression of NMHase

2.1 Conventional Methods

The 3.7 kb long SalI fragment (FIG. 2) was cloned into the commercially available vector pUC19 (Boehringer Mannheim GmbH). Subsequently the NMHase gene was completed by cloning in the EcoRI fragment of FIG. 3. However, such a construct does not lead to the expression of active NMHase.

An attempt to achieve expression of this construct by cloning under the control of an inducible tac promoter and inducing the tac promoter in the usual way (incubation at 37° C., complete medium and complete induction of the tac promoter) also failed. For this the plasmid pKK177-3 (DSM 3062) was cleaved with EcoRI and HindIII and ligated with a polylinker cut out of pUC19 by means of EcoRI and HindIII. The plasmid which forms was denoted pBP177-4. Subsequently the plasmid pBP177-4 was cleaved with EcoRI and KpnI and combined with a 2.5 kb C-terminal NMHase fragment (also cleaved with EcoRI and KpnI) to form the plasmid pBP008 (FIG. 5).

The plasmid pBP008 was cleaved with the enzymes XhoI and EcoRI and the resulting large (5 kb) fragment was combined with a 1.5 kb fragment from the NMHase N-terminus which has the end-cleavage sites AatII and XhoI and with an EcoRI-AatII linker (see FIG. 4) to form plasmid pBP009 (FIG. 6). A protein whose molecular weight approximately corresponds to that of NMHase was expressed in *E. coli* cells which were transformed with this plasmid. However, no enzymatic activity could be detected.

2.2 Process According to the Present Invention

First a C-terminal extension of the NMHase was carried out. The plasmid pBP009 (FIG. 6) was cleaved for this with the enzymes XhoI and SmaI and a resulting 5.5 kb DNA fragment is isolated which contains the tac promoter, the N-terminal region of NMHase and the ampicillin resistance gene. This fragment was combined with a C-terminal NMHase fragment from pBR328 which has the end-cleavage sites EcoRI (blunt ends by treatment with Klenow polymerase) and XhoI to form plasmid pBP010 (FIG. pBP010 is able to express NMHase.

In the next step the NMHase gene was brought under the control of the mgl promoter from Salmonella typhimurium (described in WO 88/09373). For this the plasmid pPZ07/mgllac (described in WO 88/09373) was cleaved with the enzymes NcoI and AatII and a 2.9 kb long DNA fragment was isolated therefrom which contains the mgl promoter. This fragment was combined with a NcoI-AatII linker to form plasmid pBP011 (FIG. 8).

Plasmid pBP011 was cleaved with EcoRI, it was treated with Klenow DNA polymerase in order to produce blunt ends and re-cleaved with AatII. Subsequently a resulting 0.8 kb long DNA fragment with a blunt end and an AatII end which contains the mgl promoter and the linker fragment was isolated (FIG. 8).

Plasmid pBP010 was cleaved with NdeI and treated with Klenow DNA polymerase in order to produce blunt fragment ends. Subsequently these fragments were cleaved with XhoI and a 4.9 kb long fragment was isolated which contains the C-terminal region of the NMHase gene (FIG. 9).

Plasmid pBP010 was also cleaved with XhoI and AatII in the process of which a 1.5 kb long fragment could be isolated which contains the N-terminal region of the NMHase gene (FIG. 9).

Both fragments from plasmid pBP010 (4.9 kb and 1.5 kb) were ligated with the 0.8 kb fragment from pBP011 which contains the mgl promoter. The resulting plasmid was denoted pBP006 (FIG. 10) and is capable of expressing NMHase.

EXAMPLE 3

Fermentation and Accumulation of Recombinant NMHase in *E. coli*

*E. coli* HB101 cells (DSM 1607) were transformed with the NMHase expression plasmid pBP010. In order to ensure a better regulatability of the tac promoter the cells were additionally transformed with a plasmid which is compatible with pBP010 and which contains the lacI$^q$ gene.

The lacI$^q$ gene has already been known to one skilled in the art for a long time and is easily obtainable. pACYC 177 (DSM 3693P) or plasmids derived therefrom come into consideration as the plasmid compatible with pBP010.

3.1 Growth and Preculture

2×500 ml LB medium with kaamycin and ampicillin in two 2000 ml Erlenmeyer flaks were inoculated with *E. coli* HB101/lacI$^q$/pBP010 cells. They were then incubated at 37° C. and 150 rpm (rotary shaker, Braun Certomat M). The OD at 578 nm was ca. 3.0 to 4.0 in the 10th hour at a pH of ca. 7.6.

Main fermentation:

| Nutrient medium and main culture: | |
|---|---|
| glycerol 86% | 2500 g |
| lactose | 500 g |
| NH$_4$Cl | 50 g |
| MgSO$_4$·7 H$_2$O | 50 g |
| K$_2$HPO$_4$ | 150 g |
| casein peptone | 3000 g |
| ammonia solution 25% Merck 5432 | 500 ml |
| water | 100 l |

Fermentation course:

After inoculation (1% inoculu) the culture begins to grow exponentially without dely. The temperature of the fermenter is kept at 28° C. up to an OD 578 nm of 1.400. When the desired OD is reached the temperature is decreased to 25° C., the growth slows down. In addition the oxygen transfer can be reduced. These measures are necessary in order to limit th growth and thus to counteract the formation of precipitation bodies (inclusion bodies). The correct time for the temperature shift is important, if it is carried out too soon, growth is delayed for hours, if it is carried out too late, only insoluble protein i obtained.

A further increase in activity is obtained by additionally reducing oxygen. In the fermentation with a shift in temperature the yield is ca. 2500 U/L, max 3000 U/L (150 U/OD) after 30 hours. When the amount of O$_2$ in the medium is also reduced up to 4000 U/L are obtained after 45 hours.

EXAMPLE 4

Isolation of Recombinant NMHase from *E. coli*

4.1 Measurement of the enzyme activity

The determination of the enzyme activity is carried out by means of a colorimetric test which contains carbamoyl-sarcosine hydrolase, sarcosine oxidase, peroxidase, N-methylhydantoin, 4-aminoantipyrine, tribromo-3-hydroxybenzoic acid, ATP and MgCl$_2$ in phosphate buffer, pH 7.8.

Principle of the measurement :

NMHase converts the N-methylhydantoin which was added to carbamoyl-sarcosine, carbamoyl-sarcosine hydrolase converts this to sarcosine, this is degraded by sarcosine oxidase to form glycine, formaldehyde and hydrogen peroxide. The peroxidase converts the added colour substrates into a dark-violet dye with the aid of the hydrogen peroxide which is formed. The increase in absorbance is measured at a wavelength of 546 nm. The enzyme test is described in detail in U.S. Pat. No. 4,816,393.

A unit (U) is defined as mol of carbamoyl-sarcosine formed per minute at 25° C. under measuring conditions in a coupled test with carbamoyl-sarcosine hydrolase, sarcosine oxidase and peroxidase. An activity of 0.16 U/ml is obtained in a 5 ml test culture. This corresponds to an increase by a factor of ca. 20 compared to the original culture (Arthrobacter spec. DSM 2563).

4.2 Enzyme Purification 315 g biomass (according to Example 3) resulting from 10 l fermentation culture with a total activity of 16 KU NMHase were suspended in 2 l 0.1 mol/l potassium phosphate buffer containing 10% glycerol, pH 8.0 and lysed by treatment with lysozyme and once with 700 bar high pressure dispersion. In order to remove the nucleic acids and cell debris a 10% polyethyleneimine solution G20 (Luvalgan, MW 20000) was added until no further precipitation occurs and all the NMHase activity remained in the supernatant. For this 3% v/v G 20 solution was added at room temperature, stirred for 30 minutes and afterwards centrifuged. 8% v/v in batch wet-pressed DEAE Sephadex was added to the NMHase supernatant and after stirring for 2 hours 95% of the enzyme had been adsorbed. After filtration the exchanger was washed with phosphate buffer and the NMHase was eluted with 0.5 mol/l ammonium sulphate solution containing 0.1 mol/l K-PO₄ buffer, pH 8.0. The eluate had a specific activity of 1.1 U/mg protein. Subsequently it was heated to 55° C. for ten minutes in the presence of 50 mmol/l N-methylhydantoin (final concentration) during which interfering foreign proteins were precipitated. After centrifugation the clear supernatant was further saturated to 2.2 mol/l with ammonium sulphate and the NMHase which thereby precipitates was centrifuged down. This was followed by two crystallizations, the first crystallization takes place at a protein concentration of ca. 60 mg/ml, pH 8.0, 0.1 mol/l K-PO₄ buffer, 1.27 mol/l ammonium sulphate. Prisms form after a short time. After 24 hours the crystallization was complete, only 5% NMHase remained in the centrifuged supernatant. The NMHase crystals were dissolved in 0.1 mol/l K-PO₄ buffer and after removing undissolved constituents the enzyme solution was subjected to a second crystallization (1.05 mol/l ammonium sulphate concentration). The enzyme crystals which formed overnight were collected, resuspended in buffer, dialyzed against 20 mmol/l phosphate buffer and 2 parts raffinose were added (with respect to the amount of protein) and lyophilized.

The yield was 5.8 KU NMHase=34% of the starting activity with a specific activity of 2.15 U/mg protein.

The enzyme activity was tested according to Example 4.1 after each purification step.

No catalase, creatinase, creatininase and carbamoyl-sarcosine hydrolase activities were measurable. A minimal oxidase activity (=sum of glucose oxidase, pyruvate oxidase, lactate oxidase, uricase and cholesterol oxidase) of 0.002% was noted.

The properties of the recombinant NMHase concerning the pH optimum, pH stability, temperature dependence, thermal stability, $K_M$, ATP and magnesium dependence, ammonium dependence and molecular weight corresponded to the properties of the NMHase from Arthrobacter.

EXAMPLE 5

Sequencing of the NMHse Gene

Fragments from the gene coding for NMHase were subcloned into the cloning vector M13 and sequenced according to standard techniques. The nucleic acid sequence is shown in SEQ ID NO: 1. This results in a protein with 1288 amino acids whose sequence is shown in SEQ ID NO: 2.

We claim:

1. An isolated DNA fragment, where it has (1) the nucliec acid sequence shown in SEQ ID NO: 1, (2) a sequence corresponding to the sequence of (1) within the scope of the degeneracy of the genetic code or (3) a sequence which hybridizes with a sequence complementary to the sequence from (1) or (2) under stringent conditions and which codes for a protein with N-methylhydantionase activity.

2. A cloning vector, wherein it contains one or several copies of a DNA as claimed in claim 1.

3. The cloning vector as claimed in claim 2, wherein it is a prokaryotic vector.

4. The cloning vector as claimed in claim 2, wherein it is a plasmid.

5. Plasmid pBP010.

6. The cloning vector as claimed in claim 2, wherein the DNA as claimed in claim 1 is under the control of a regulatable promoter.

7. The cloning vector as claimed in claim 6, wherein the regulatable promoter is the mgl promoter from Salmonella typhimurium.

8. Plasmid pBP006.

9. A cell which is transformed with the DNA of claim 1.

10. The cell as claimed in claim 9, wherein it is a bacterial cell.

11. The cell as claimed in claim 10, wherein it is an *E. coli* cell.

12. A process for the production of a protein with NMHase activity, wherein
    the transformed cells of claim 9 are cultured in a suitable medium and a protein having NMHase activity is isolated from the medium or the cells.

13. The process as claimed in claim 12, wherein an *E. coli* cell is used as the cell.

14. The process as claimed in claim 12, wherein a DNA or a vector is used for the transformation in which the gene coding for a protein with NMHase activity is under the control of a regulatable promoter.

15. The process as claimed in claim 12, wherein the transformed cell is cultured under suboptimal growth conditions.

16. The process as claimed in claim 15, wherein the cells are cultured in a minimal medium.

17. The process as claimed in claim 15 or 16, wherein the cells are incubated at a maximum incubation temperature of 30° C.

18. The process as claimed in claim 12, wherein the transfer of oxygen into the medium is reduced.

19. The process as claimed in claim 12, wherein the induction of the regulatable promoter is only carried out incompletely.

20. The process as claimed in claim 12, wherein after step (3), approximately 3.8 nmol of N-methylhydantoin per unit (U) of the protein having NMHase activity is added to the protein having NMHase for stabilization.

21. The process as claimed in claim 20, wherein the protein having NMHase activity is incubated with a N-methylhydantoin solution at a temperature above 30° C.

22. A process for the production of a protein with NMHase activity, wherein
   (1) a *E. coli* gram negative bacteria is transformed with a vector as claimed in one of the claims 6 to 8,
   (2) the transformed bacteria are cultured in a suitable medium and
   (3) a protein having NMHase activity is isolated from the medium or the bacteria.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 3867 base pairs
        ( B ) TYPE: nucleic acid
        ( C ) STRANDEDNESS: double
        ( D ) TOPOLOGY: linear ( i i ) MOLECULE TYPE: DNA (genomic)

( i x ) FEATURE:
        ( A ) NAME/KEY: CDS
        ( B ) LOCATION: 1..3867
        ( D ) OTHER INFORMATION: /product="Protein
        N-methylhydantoinase"

( x i ) SEQUENCE DESCRIPTION: SEQ ID NO:1:

```
ATG  AAG  CGC  ATC  GGA  GTA  GAC  GTC  GGC  GGC  ACC  TTC  ACC  GAC  TTG  TAT         48
Met  Lys  Arg  Ile  Gly  Val  Asp  Val  Gly  Gly  Thr  Phe  Thr  Asp  Leu  Tyr
  1             5                  10                  15

TTT  TCG  GAC  GAT  GAC  CAG  CGC  ATC  GCT  GTG  GTC  GAG  AAG  GTT  CCC  TCG         96
```

|  |  |  |  |  |  |  |  |  |  |  |  |  |  |  |  |
|---|---|---|---|---|---|---|---|---|---|---|---|---|---|---|---|
| Phe | Ser | Asp | Asp<br>20 | Asp | Gln | Arg | Ile<br>25 | Ala | Val | Val | Glu<br>30 | Lys | Val | Pro | Ser |

| ACT | CCT | CAC | GAC | CCG | TCC | GAG | GCC | GTG | ATC | AAT | GGC | ATT | AAG | AAG | CTC | 144 |
|---|---|---|---|---|---|---|---|---|---|---|---|---|---|---|---|---|
| Thr | Pro | His<br>35 | Asp | Pro | Ser | Glu<br>40 | Ala | Val | Ile | Asn | Gly<br>45 | Ile | Lys | Lys | Leu | |

| TGT | GAG | AAG | GCG | GGA | GTG | TCT | CTG | TCA | GAG | ATC | GAC | CAG | CTG | GTC | CAT | 192 |
|---|---|---|---|---|---|---|---|---|---|---|---|---|---|---|---|---|
| Cys | Glu<br>50 | Lys | Ala | Gly | Val | Ser<br>55 | Leu | Ser | Glu | Ile | Asp<br>60 | Gln | Leu | Val | His | |

| GGG | ACT | ACG | GTA | GCC | ACC | AAC | ACC | GCA | CTA | ACG | CAC | ACT | GGC | GCG | GAA | 240 |
|---|---|---|---|---|---|---|---|---|---|---|---|---|---|---|---|---|
| Gly<br>65 | Thr | Thr | Val | Ala | Thr<br>70 | Asn | Thr | Ala | Leu | Thr<br>75 | His | Thr | Gly | Ala | Glu<br>80 | |

| GTC | GGG | ATG | ATT | ACT | ACC | GAG | GGC | TTC | CGG | GAT | ATC | TTG | CAT | ATC | GCC | 288 |
|---|---|---|---|---|---|---|---|---|---|---|---|---|---|---|---|---|
| Val | Gly | Met | Ile | Thr<br>85 | Thr | Glu | Gly | Phe | Arg<br>90 | Asp | Ile | Leu | His | Ile<br>95 | Ala | |

| AGG | CAC | AAA | AAA | CCG | CAT | AAT | TTC | TCT | CTG | CAG | CAG | GAT | CTG | CCG | TGG | 336 |
|---|---|---|---|---|---|---|---|---|---|---|---|---|---|---|---|---|
| Arg | His | Lys | Lys<br>100 | Pro | His | Asn | Phe | Ser<br>105 | Leu | Gln | Gln | Asp | Leu<br>110 | Pro | Trp | |

| CAG | ACC | AAA | CCA | CTG | ATC | AAG | CGC | CGG | TAT | CGG | CTC | ACC | GTT | AAG | GAA | 384 |
|---|---|---|---|---|---|---|---|---|---|---|---|---|---|---|---|---|
| Gln | Thr | Lys<br>115 | Pro | Leu | Ile | Lys | Arg<br>120 | Arg | Tyr | Arg | Leu | Thr<br>125 | Val | Lys | Glu | |

| CGT | ATC | ACC | GCG | CCG | CAC | GGT | GAG | ATC | CTG | GTC | CCT | TTG | GAT | GAG | GAT | 432 |
|---|---|---|---|---|---|---|---|---|---|---|---|---|---|---|---|---|
| Arg | Ile | Thr | Ala<br>130 | Pro | His | Gly | Glu | Ile<br>135 | Leu | Val | Pro | Leu | Asp<br>140 | Glu | Asp | |

| GAG | GTC | CGA | CAG | AGA | GTG | CGT | GAG | CTC | AAG | ACA | GCT | GGC | GTG | CAG | GCC | 480 |
|---|---|---|---|---|---|---|---|---|---|---|---|---|---|---|---|---|
| Glu<br>145 | Val | Arg | Gln | Arg | Val<br>150 | Arg | Glu | Leu | Lys | Thr<br>155 | Ala | Gly | Val | Gln | Ala<br>160 | |

| ATC | GCT | GTA | TGT | CTG | TTG | CAT | TCG | TAT | TTG | AAC | CCG | GAG | CAC | GAG | CAG | 528 |
|---|---|---|---|---|---|---|---|---|---|---|---|---|---|---|---|---|
| Ile | Ala | Val | Cys | Leu<br>165 | Leu | His | Ser | Tyr | Leu<br>170 | Asn | Pro | Glu | His | Glu<br>175 | Gln | |

| CGA | ATC | GGC | GAG | ATC | GTC | AAT | GAG | GAA | TTC | CCC | GAG | GCG | TAT | CTT | TCC | 576 |
|---|---|---|---|---|---|---|---|---|---|---|---|---|---|---|---|---|
| Arg | Ile | Gly | Glu<br>180 | Ile | Val | Asn | Glu | Glu<br>185 | Phe | Pro | Glu | Ala | Tyr<br>190 | Leu | Ser | |

| CTG | TCT | TCT | GAA | ATT | GTG | CCT | CTA | TAT | CGA | GAG | TAT | GAA | CGA | TTC | TCA | 624 |
|---|---|---|---|---|---|---|---|---|---|---|---|---|---|---|---|---|
| Leu | Ser | Ser<br>195 | Glu | Ile | Val | Pro | Leu<br>200 | Tyr | Arg | Glu | Tyr | Glu<br>205 | Arg | Phe | Ser | |

| ACT | ACC | GCA | TTA | AAT | GCC | TAC | GTT | GGC | CCT | AGG | GTC | TCG | CGC | TAC | CTG | 672 |
|---|---|---|---|---|---|---|---|---|---|---|---|---|---|---|---|---|
| Thr | Thr | Ala<br>210 | Leu | Asn | Ala | Tyr | Val<br>215 | Gly | Pro | Arg | Val | Ser<br>220 | Arg | Tyr | Leu | |

| CAT | CGC | CTG | CAG | GAG | CAG | GCC | GAA | AAT | TTG | GGG | TAC | CAG | CGC | GAA | ATC | 720 |
|---|---|---|---|---|---|---|---|---|---|---|---|---|---|---|---|---|
| His | Arg | Leu<br>225 | Gln | Glu | Gln | Ala | Glu<br>230 | Asn | Leu | Gly | Tyr | Gln<br>235 | Arg | Glu | Ile<br>240 | |

| CTG | CTA | ATG | CAG | TCT | TCA | GGC | GGC | ATG | GTG | CCT | ATT | GGT | GAA | GCT | GCG | 768 |
|---|---|---|---|---|---|---|---|---|---|---|---|---|---|---|---|---|
| Leu | Leu | Met | Gln | Ser<br>245 | Ser | Gly | Gly | Met | Val<br>250 | Pro | Ile | Gly | Glu | Ala<br>255 | Ala | |

| AAA | CGG | CCG | GTG | ACG | TTG | ATG | ATG | TCC | GGT | CCA | GTG | GGA | GGT | CTG | ATC | 816 |
|---|---|---|---|---|---|---|---|---|---|---|---|---|---|---|---|---|
| Lys | Arg | Pro | Val<br>260 | Thr | Leu | Met | Met | Ser<br>265 | Gly | Pro | Val | Gly | Gly<br>270 | Leu | Ile | |

| GGT | GGT | ATG | TGG | GCT | GCT | AAG | CAG | TCT | GGA | TTT | GAG | AAC | GTG | GTT | ACC | 864 |
|---|---|---|---|---|---|---|---|---|---|---|---|---|---|---|---|---|
| Gly | Gly | Met<br>275 | Trp | Ala | Ala | Lys | Gln<br>280 | Ser | Gly | Phe | Glu | Asn<br>285 | Val | Val | Thr | |

| CTA | GAT | ATC | GGG | GGC | ACC | TCT | GCG | GAT | ATC | GGC | GTT | GCC | TAC | CAG | GGT | 912 |
|---|---|---|---|---|---|---|---|---|---|---|---|---|---|---|---|---|
| Leu | Asp | Ile | Gly<br>290 | Gly | Thr | Ser | Ala<br>295 | Asp | Ile | Gly | Val | Ala<br>300 | Tyr | Gln | Gly | |

| GAG | TTG | CGC | ATG | CGC | CAC | CTG | CTG | GAC | ACG | AAG | ATC | GGT | GAT | CAT | CAA | 960 |
|---|---|---|---|---|---|---|---|---|---|---|---|---|---|---|---|---|
| Glu<br>305 | Leu | Arg | Met | Arg | His<br>310 | Leu | Leu | Asp | Thr | Lys<br>315 | Ile | Gly | Asp | His | Gln<br>320 | |

| GCC | ATG | GTT | CCC | ATG | GTG | GAT | ATC | GAC | ACT | ATC | GGT | GCC | GGC | GGT | GGT | 1008 |
|---|---|---|---|---|---|---|---|---|---|---|---|---|---|---|---|---|
| Ala | Met | Val | Pro | Met<br>325 | Val | Asp | Ile | Asp | Thr<br>330 | Ile | Gly | Ala | Gly | Gly<br>335 | Gly | |

| TCG | ATC | GCC | TAT | GTT | GAT | GCT | GGT | GGC | GTC | TTC | CGC | GTG | GGC | CCC | CAG | 1056 |
|---|---|---|---|---|---|---|---|---|---|---|---|---|---|---|---|---|
| Ser | Ile | Ala | Tyr<br>340 | Val | Asp | Ala | Gly<br>345 | Gly | Val | Phe | Arg | Val<br>350 | Gly | Pro | Gln | |

| | | | | | | | | | | | | | | | | |
|---|---|---|---|---|---|---|---|---|---|---|---|---|---|---|---|---|
| TCA | GCT | GGT | GCT | GTT | CCG | GGG | CCG | GTC | TGT | TAC | GGC | CGC | GGT | GGA | ACG | 1104 |
| Ser | Ala | Gly | Ala | Val | Pro | Gly | Pro | Val | Cys | Tyr | Gly | Arg | Gly | Gly | Thr | |
| | | 355 | | | | 360 | | | | | | 365 | | | | |
| GAA | CCA | ACG | TCA | ACC | GAT | GCT | CAG | GTA | CTG | CTC | GGA | AGG | ATG | CGT | CCA | 1152 |
| Glu | Pro | Thr | Ser | Thr | Asp | Ala | Gln | Val | Leu | Leu | Gly | Arg | Met | Arg | Pro | |
| | 370 | | | | | 375 | | | | | 380 | | | | | |
| GAC | AGA | ATT | CTG | GCC | GGC | TCG | GGT | TTG | GAC | ATG | GAT | CTC | GAC | CGT | GCC | 1200 |
| Asp | Arg | Ile | Leu | Ala | Gly | Ser | Gly | Leu | Asp | Met | Asp | Leu | Asp | Arg | Ala | |
| 385 | | | | | 390 | | | | | 395 | | | | | 400 | |
| CGC | GCT | GCC | ATG | CAA | GGA | CTG | GCC | GAC | AAG | CTC | GGC | ATG | TCC | ATC | GAA | 1248 |
| Arg | Ala | Ala | Met | Gln | Gly | Leu | Ala | Asp | Lys | Leu | Gly | Met | Ser | Ile | Glu | |
| | | | | 405 | | | | | 410 | | | | | 415 | | |
| GAA | GCG | GCA | CTG | GGT | GCG | CTT | CAG | ATC | CAG | AAG | TTT | GGA | ATG | ACC | CAG | 1296 |
| Glu | Ala | Ala | Leu | Gly | Ala | Leu | Gln | Ile | Gln | Lys | Phe | Gly | Met | Thr | Gln | |
| | | | 420 | | | | | 425 | | | | | 430 | | | |
| GCC | ATT | GAG | CAG | AAC | TCA | GTT | CGC | CGG | GGG | TAT | GAT | CCG | CGA | GAT | TTC | 1344 |
| Ala | Ile | Glu | Gln | Asn | Ser | Val | Arg | Arg | Gly | Tyr | Asp | Pro | Arg | Asp | Phe | |
| | | 435 | | | | | 440 | | | | | 445 | | | | |
| ACT | CTT | GTC | GCT | GCC | GGT | GGA | GCT | GGC | GCC | TTG | TTC | GCC | TGT | GAG | ATT | 1392 |
| Thr | Leu | Val | Ala | Ala | Gly | Gly | Ala | Gly | Ala | Leu | Phe | Ala | Cys | Glu | Ile | |
| | 450 | | | | | 455 | | | | | 460 | | | | | |
| GCT | GCT | GAA | CTC | GAA | GTG | CCG | CAC | GTA | CTG | GTC | CCG | GCT | CAT | CCA | GGC | 1440 |
| Ala | Ala | Glu | Leu | Glu | Val | Pro | His | Val | Leu | Val | Pro | Ala | His | Pro | Gly | |
| 465 | | | | | 470 | | | | | 475 | | | | | 480 | |
| ATC | ATC | GCA | GGT | ATC | GGG | TTG | CTG | GCC | ACG | GAT | GAG | CAA | TAC | GAG | TTT | 1488 |
| Ile | Ile | Ala | Gly | Ile | Gly | Leu | Leu | Ala | Thr | Asp | Glu | Gln | Tyr | Glu | Phe | |
| | | | | 485 | | | | | 490 | | | | | 495 | | |
| GTG | GCA | ACC | AAC | CGG | TTC | AGC | TTT | GCT | TTC | CGT | GAC | GCT | GCG | GTC | ATC | 1536 |
| Val | Ala | Thr | Asn | Arg | Phe | Ser | Phe | Ala | Phe | Arg | Asp | Ala | Ala | Val | Ile | |
| | | | 500 | | | | | 505 | | | | | 510 | | | |
| CAA | GCG | TCC | TAC | GAG | CAG | CTC | GAG | CGC | GAA | CGT | AAC | GCT | CAA | CTG | GAT | 1584 |
| Gln | Ala | Ser | Tyr | Glu | Gln | Leu | Glu | Arg | Glu | Arg | Asn | Ala | Gln | Leu | Asp | |
| | | 515 | | | | | 520 | | | | | 525 | | | | |
| GCC | GAA | GAA | GTC | CCC | GCC | GAA | CGG | CGC | AAA | ATT | GTT | TGG | CTG | CGT | GAC | 1632 |
| Ala | Glu | Glu | Val | Pro | Ala | Glu | Arg | Arg | Lys | Ile | Val | Trp | Leu | Arg | Asp | |
| | 530 | | | | | 535 | | | | | 540 | | | | | |
| GCT | CGA | TAT | GAG | GGC | CAA | GGC | TAT | GAG | ATC | CGC | TTC | GTC | GTA | CCC | GAG | 1680 |
| Ala | Arg | Tyr | Glu | Gly | Gln | Gly | Tyr | Glu | Ile | Arg | Phe | Val | Val | Pro | Glu | |
| 545 | | | | | 550 | | | | | 555 | | | | | 560 | |
| GGG | CCG | GTC | ACT | ACC | GCA | TGG | TTG | GAC | CAA | GCA | GAA | GCC | GCT | TTC | CAC | 1728 |
| Gly | Pro | Val | Thr | Thr | Ala | Trp | Leu | Asp | Gln | Ala | Glu | Ala | Ala | Phe | His | |
| | | | | 565 | | | | | 570 | | | | | 575 | | |
| GAT | GCC | CAC | TTC | GAG | GAA | TAC | GGC | CAC | CGC | TTT | AAG | GGC | GGC | ACC | GTA | 1776 |
| Asp | Ala | His | Phe | Glu | Glu | Tyr | Gly | His | Arg | Phe | Lys | Gly | Gly | Thr | Val | |
| | | | 580 | | | | | 585 | | | | | 590 | | | |
| GAG | GTG | ATC | AAT | ATC | AGG | GTG | GAA | GCC | CGT | GCC | GTT | ATG | GAT | GAA | CTG | 1824 |
| Glu | Val | Ile | Asn | Ile | Arg | Val | Glu | Ala | Arg | Ala | Val | Met | Asp | Glu | Leu | |
| | | 595 | | | | | 600 | | | | | 605 | | | | |
| CCC | ACG | CCA | GAA | GCG | ACG | CAG | TCA | GGC | TCA | CTT | GAA | AAT | GCG | TTG | GTG | 1872 |
| Pro | Thr | Pro | Glu | Ala | Thr | Gln | Ser | Gly | Ser | Leu | Glu | Asn | Ala | Leu | Val | |
| | 610 | | | | | 615 | | | | | 620 | | | | | |
| GAG | ACC | CGC | CCT | GTA | ACT | TTC | CAG | CAA | GCA | GGT | AAG | CCT | GTC | ACC | TTG | 1920 |
| Glu | Thr | Arg | Pro | Val | Thr | Phe | Gln | Gln | Ala | Gly | Lys | Pro | Val | Thr | Leu | |
| 625 | | | | | 630 | | | | | 635 | | | | | 640 | |
| GAC | ACC | GGA | TTC | TAC | GAC | CGG | GCC | AAG | ATG | GGA | ATC | GGA | ACC | ACG | TTC | 1968 |
| Asp | Thr | Gly | Phe | Tyr | Asp | Arg | Ala | Lys | Met | Gly | Ile | Gly | Thr | Thr | Phe | |
| | | | | 645 | | | | | 650 | | | | | 655 | | |
| GCC | GGA | CCG | GTG | GTC | ATC | GAG | CAG | TAC | GAC | TCC | ACC | ACA | GTG | ATT | CCT | 2016 |
| Ala | Gly | Pro | Val | Val | Ile | Glu | Gln | Tyr | Asp | Ser | Thr | Thr | Val | Ile | Pro | |
| | | | 660 | | | | | 665 | | | | | 670 | | | |
| CCA | GGT | TTC | ACC | GGG | ACG | GTG | GAT | GAT | GCC | GGC | AAC | CTG | GTC | ATC | GCT | 2064 |

```
                Pro  Gly  Phe  Thr  Gly  Thr  Val  Asp  Asp  Ala  Gly  Asn  Leu  Val  Ile  Ala
                     675            680                          685

TGC CCA GCG GTC ACC CAG ACT GTG GAG AAG CTG GCC ACC CCG ATT CTC                              2112
Cys Pro Ala Val Thr Gln Thr Val Glu Lys Leu Ala Thr Pro Ile Leu
    690             695                 700

ATG CGC GTC ATC GGC GGC GCG TTG AAC TCG GCG GCC AAA GAA ATG GCT                              2160
Met Arg Val Ile Gly Gly Ala Leu Asn Ser Ala Ala Lys Glu Met Ala
705             710                 715                 720

TCG GTG CTT TTC CGC ATG TCT TAC TCA TCG ATC ATC CGC GAA TCG GAG                              2208
Ser Val Leu Phe Arg Met Ser Tyr Ser Ser Ile Ile Arg Glu Ser Glu
                    725                 730                 735

GAT CTG GGA GCT GGC CTC TTC GAT AAG GAC GGA AAC GTC CTG GCC GAA                              2256
Asp Leu Gly Ala Gly Leu Phe Asp Lys Asp Gly Asn Val Leu Ala Glu
                740                 745                 750

TCA GAT TCC ACC CCA ATG TTC ATG GGC TCC ATG CCG AAA ATT GTC AAA                              2304
Ser Asp Ser Thr Pro Met Phe Met Gly Ser Met Pro Lys Ile Val Lys
        755                 760                 765

GGT GTC ATC TCT GTC CTG GGC GAC GAC ATC CAT GAT GGC GAC GTC ATC                              2352
Gly Val Ile Ser Val Leu Gly Asp Asp Ile His Asp Gly Asp Val Ile
        770                 775                 780

TTG CAC AAT GAT CCG TAC TTG GGG GCT ACG CAC TCC CCG GAT GTT GCA                              2400
Leu His Asn Asp Pro Tyr Leu Gly Ala Thr His Ser Pro Asp Val Ala
785             790                 795                 800

ATC ATC GAA CCC ATC TTC CAC GAT GGA GAA CTC GTC GGT TTC GCT GGA                              2448
Ile Ile Glu Pro Ile Phe His Asp Gly Glu Leu Val Gly Phe Ala Gly
                805                 810                 815

GCC TCC GGG CAA CTG ATC GAT AAC GGT GGC GCA TTT TCT GGA CTG ATG                              2496
Ala Ser Gly Gln Leu Ile Asp Asn Gly Gly Ala Phe Ser Gly Leu Met
                820                 825                 830

GTA GAT ATT CAG GAC GTG CAG TCC GAA GGA ACC ATC TTC CGG GCG GTG                              2544
Val Asp Ile Gln Asp Val Gln Ser Glu Gly Thr Ile Phe Arg Ala Val
            835                 840                 845

AAG GTC TAT GAG AAG GGT GTT CGT CAG GAG TCA CTG ATC CGG CAC ATC                              2592
Lys Val Tyr Glu Lys Gly Val Arg Gln Glu Ser Leu Ile Arg His Ile
    850                 855                 860

CTG AAC AAC ACT CGC ACA CCT ACC TCT AAC GAG GGC GAC TTC CAG GCA                              2640
Leu Asn Asn Thr Arg Thr Pro Thr Ser Asn Glu Gly Asp Phe Gln Ala
865             870                 875                 880

ATG ATC GCC GCG TGT GAT CTG GCC AAG TCC CGT TAC TTG GCC CTG GTC                              2688
Met Ile Ala Ala Cys Asp Leu Ala Lys Ser Arg Tyr Leu Ala Leu Val
                885                 890                 895

GAG CGG TAT GGC CGA GAC TCG GTT CGT GAC GCC GGG CAG TTC TGG ATC                              2736
Glu Arg Tyr Gly Arg Asp Ser Val Arg Asp Ala Gly Gln Phe Trp Ile
            900                 905                 910

GAT TAT TCA GAG CGT ATC GTA CGC CAG GAA ATC GCT AAG ATT CCG GAT                              2784
Asp Tyr Ser Glu Arg Ile Val Arg Gln Glu Ile Ala Lys Ile Pro Asp
        915                 920                 925

GGT GTG TAC GAA ACC GAG ACA GGC TAC TTG GAC GAT GAC GGA CGC AAC                              2832
Gly Val Tyr Glu Thr Glu Thr Gly Tyr Leu Asp Asp Asp Gly Arg Asn
    930                 935                 940

TAC GGC AAA AAG CTT CCC ATC GTC GTG AAG GTC ATT GTT GAG GGC GAT                              2880
Tyr Gly Lys Lys Leu Pro Ile Val Val Lys Val Ile Val Glu Gly Asp
945             950                 955                 960

GAG ATT ACC TAC GAC CTC ACA GGA TCC TCC GCA CAG GTG CCG ACG GCC                              2928
Glu Ile Thr Tyr Asp Leu Thr Gly Ser Ser Ala Gln Val Pro Thr Ala
                965                 970                 975

TAC AAC TGC GCA TTC GAA GGA ACC ACT GTC TCG GCG TTC ACG TTC ATC                              2976
Tyr Asn Cys Ala Phe Glu Gly Thr Thr Val Ser Ala Phe Thr Phe Ile
            980                 985                 990

ACC CGC ATG ATG TTC TTG GAT GAG GTC GCG TTC CCG GTA TTC GTC CCA                              3024
Thr Arg Met Met Phe Leu Asp Glu Val Ala Phe Pro Val Phe Val Pro
        995                 1000                1005
```

```
CAG AAC GAG GGC ATG CTC AAA GCG TTG AAG GTG ATC GCA CCG AAG GGA            3072
Gln Asn Glu Gly Met Leu Lys Ala Leu Lys Val Ile Ala Pro Lys Gly
    1010                1015                1020

ACT ATC TTC AAT CCG AAC TAC CCG GCG GCT ACT TTT AGC AGA TTC TCC            3120
Thr Ile Phe Asn Pro Asn Tyr Pro Ala Ala Thr Phe Ser Arg Phe Ser
1025                1030                1035                1040

CAG GTG CAG CGT GCC GTC GAC CTA GCG TTG CGA GCG CTG GCC CCG GTC            3168
Gln Val Gln Arg Ala Val Asp Leu Ala Leu Arg Ala Leu Ala Pro Val
                1045                1050                1055

ATG CCC GAA CGA GTT ACT GCC GGA AAC TCG GCC CAT ATC CAC TTC ATG            3216
Met Pro Glu Arg Val Thr Ala Gly Asn Ser Ala His Ile His Phe Met
            1060                1065                1070

TCC TAC TCT GGC TGG GAC GAA AAG CAA GGT GAG TAC TGG GTC TAT CTG            3264
Ser Tyr Ser Gly Trp Asp Glu Lys Gln Gly Glu Tyr Trp Val Tyr Leu
        1075                1080                1085

GAA GTC AAT GAG GGT TCC TAT GGA GCT CGC CAG GAC TCC GAC GGC CCA            3312
Glu Val Asn Glu Gly Ser Tyr Gly Ala Arg Gln Asp Ser Asp Gly Pro
    1090                1095                1100

GAT TCG GTT GAC AAC CTC ATC GCC AAC ACC CGC AAT AAT CCG ATC GAA            3360
Asp Ser Val Asp Asn Leu Ile Ala Asn Thr Arg Asn Asn Pro Ile Glu
1105                1110                1115                1120

GAA CTC GAA TGG CGG TTC CCG ATG CGT ACT GAC CGC TAC GAG CTA CGC            3408
Glu Leu Glu Trp Arg Phe Pro Met Arg Thr Asp Arg Tyr Glu Leu Arg
                1125                1130                1135

GAG GAT CCG GCC GCC GCC GGC GAA TAC CGT GGC GGA ATC GGC ATT GTC            3456
Glu Asp Pro Ala Ala Ala Gly Glu Tyr Arg Gly Gly Ile Gly Ile Val
            1140                1145                1150

CGG GAG AAC ACC TTC TTG GAG GAT ACT GCG GTG ACC TGC GAG GGC GAA            3504
Arg Glu Asn Thr Phe Leu Glu Asp Thr Ala Val Thr Cys Glu Gly Glu
        1155                1160                1165

CGT CAC GAT TCA GAT GTC CCA TGG GGC GCC TAT GGC GGC CAC GAC GGT            3552
Arg His Asp Ser Asp Val Pro Trp Gly Ala Tyr Gly Gly His Asp Gly
    1170                1175                1180

CTG AAT GCG TCC CTG ATA AAG AAC CCA GGC CGC GAC GGG GAA GAG TCC            3600
Leu Asn Ala Ser Leu Ile Lys Asn Pro Gly Arg Asp Gly Glu Glu Ser
1185                1190                1195                1200

TGG CCG TCA AAG GTC ACC GGT CGT CAG TTG CAA GCC GGT GAT TCC TTG            3648
Trp Pro Ser Lys Val Thr Gly Arg Gln Leu Gln Ala Gly Asp Ser Leu
                1205                1210                1215

CAG ATC ACG GTA CCT AGC GGC GGT GGT TTC GGA GAC CCG CTC AAG CGC            3696
Gln Ile Thr Val Pro Ser Gly Gly Gly Phe Gly Asp Pro Leu Lys Arg
            1220                1225                1230

AAC CCA TTG CAG GTT CTC GAA GAT GTG CTC GAT GGA TTC ACC ACC ACC            3744
Asn Pro Leu Gln Val Leu Glu Asp Val Leu Asp Gly Phe Thr Thr Thr
        1235                1240                1245

GAA GCC GCT TCC AGG GAC TAC GGT GTG ATT CTC AAA ACG GTC AAT GGT            3792
Glu Ala Ala Ser Arg Asp Tyr Gly Val Ile Leu Lys Thr Val Asn Gly
    1250                1255                1260

CAA CTC ACC GTC GAT CTA GCG GCC ACC GCT GTA AAA CGG GAG AAC GCA            3840
Gln Leu Thr Val Asp Leu Ala Ala Thr Ala Val Lys Arg Glu Asn Ala
1265                1270                1275                1280

GTC TCT GAG CTC AGC CAC ACC AAC TGA                                        3867
Val Ser Glu Leu Ser His Thr Asn
                1285
```

( 2 ) INFORMATION FOR SEQ ID NO:2:

( i ) SEQUENCE CHARACTERISTICS:
        ( A ) LENGTH: 1288 amino acids
        ( B ) TYPE: amino acid
        (.D ) TOPOLOGY: linear ( i i ) MOLECULE TYPE: protein ( x i ) SEQUENCE DESCRIPTION: SEQ ID NO:2:

```
Met Lys Arg Ile Gly Val Asp Val Gly Gly Thr Phe Thr Asp Leu Tyr
 1               5                  10                   15

Phe Ser Asp Asp Asp Gln Arg Ile Ala Val Val Glu Lys Val Pro Ser
              20                  25                  30

Thr Pro His Asp Pro Ser Glu Ala Val Ile Asn Gly Ile Lys Lys Leu
          35                  40                  45

Cys Glu Lys Ala Gly Val Ser Leu Ser Glu Ile Asp Gln Leu Val His
     50                  55                  60

Gly Thr Thr Val Ala Thr Asn Thr Ala Leu Thr His Thr Gly Ala Glu
 65                  70                  75                   80

Val Gly Met Ile Thr Thr Glu Gly Phe Arg Asp Ile Leu His Ile Ala
                 85                  90                  95

Arg His Lys Lys Pro His Asn Phe Ser Leu Gln Gln Asp Leu Pro Trp
             100                 105                 110

Gln Thr Lys Pro Leu Ile Lys Arg Arg Tyr Arg Leu Thr Val Lys Glu
         115                 120                 125

Arg Ile Thr Ala Pro His Gly Glu Ile Leu Val Pro Leu Asp Glu Asp
     130                 135                 140

Glu Val Arg Gln Arg Val Arg Glu Leu Lys Thr Ala Gly Val Gln Ala
145                 150                 155                 160

Ile Ala Val Cys Leu Leu His Ser Tyr Leu Asn Pro Glu His Glu Gln
                 165                 170                 175

Arg Ile Gly Glu Ile Val Asn Glu Phe Pro Glu Ala Tyr Leu Ser
             180                 185                 190

Leu Ser Ser Glu Ile Val Pro Leu Tyr Arg Glu Tyr Glu Arg Phe Ser
         195                 200                 205

Thr Thr Ala Leu Asn Ala Tyr Val Gly Pro Arg Val Ser Arg Tyr Leu
     210                 215                 220

His Arg Leu Gln Glu Gln Ala Glu Asn Leu Gly Tyr Gln Arg Glu Ile
225                 230                 235                 240

Leu Leu Met Gln Ser Ser Gly Gly Met Val Pro Ile Gly Glu Ala Ala
                 245                 250                 255

Lys Arg Pro Val Thr Leu Met Met Ser Gly Pro Val Gly Gly Leu Ile
             260                 265                 270

Gly Gly Met Trp Ala Ala Lys Gln Ser Gly Phe Glu Asn Val Val Thr
         275                 280                 285

Leu Asp Ile Gly Gly Thr Ser Ala Asp Ile Gly Val Ala Tyr Gln Gly
     290                 295                 300

Glu Leu Arg Met Arg His Leu Leu Asp Thr Lys Ile Gly Asp His Gln
305                 310                 315                 320

Ala Met Val Pro Met Val Asp Ile Asp Thr Ile Gly Ala Gly Gly Gly
                 325                 330                 335

Ser Ile Ala Tyr Val Asp Ala Gly Gly Val Phe Arg Val Gly Pro Gln
             340                 345                 350

Ser Ala Gly Ala Val Pro Gly Pro Val Cys Tyr Gly Arg Gly Gly Thr
         355                 360                 365

Glu Pro Thr Ser Thr Asp Ala Gln Val Leu Leu Gly Arg Met Arg Pro
     370                 375                 380

Asp Arg Ile Leu Ala Gly Ser Gly Leu Asp Met Asp Leu Asp Arg Ala
385                 390                 395                 400

Arg Ala Ala Met Gln Gly Leu Ala Asp Lys Leu Gly Met Ser Ile Glu
                 405                 410                 415
```

```
Glu Ala Ala Leu Gly Ala Leu Gln Ile Gln Lys Phe Gly Met Thr Gln
            420                 425                 430
Ala Ile Glu Gln Asn Ser Val Arg Arg Gly Tyr Asp Pro Arg Asp Phe
        435                 440                 445
Thr Leu Val Ala Ala Gly Gly Ala Gly Ala Leu Phe Ala Cys Glu Ile
            450                 455                 460
Ala Ala Glu Leu Glu Val Pro His Val Leu Val Pro Ala His Pro Gly
465                 470                 475                 480
Ile Ile Ala Gly Ile Gly Leu Leu Ala Thr Asp Glu Gln Tyr Glu Phe
                485                 490                 495
Val Ala Thr Asn Arg Phe Ser Phe Ala Phe Arg Asp Ala Ala Val Ile
            500                 505                 510
Gln Ala Ser Tyr Glu Gln Leu Glu Arg Glu Arg Asn Ala Gln Leu Asp
        515                 520                 525
Ala Glu Glu Val Pro Ala Glu Arg Arg Lys Ile Val Trp Leu Arg Asp
    530                 535                 540
Ala Arg Tyr Glu Gly Gln Gly Tyr Glu Ile Arg Phe Val Val Pro Glu
545                 550                 555                 560
Gly Pro Val Thr Thr Ala Trp Leu Asp Gln Ala Glu Ala Ala Phe His
            565                 570                 575
Asp Ala His Phe Glu Glu Tyr Gly His Arg Phe Lys Gly Gly Thr Val
            580                 585                 590
Glu Val Ile Asn Ile Arg Val Glu Ala Arg Ala Val Met Asp Glu Leu
        595                 600                 605
Pro Thr Pro Glu Ala Thr Gln Ser Gly Ser Leu Glu Asn Ala Leu Val
    610                 615                 620
Glu Thr Arg Pro Val Thr Phe Gln Gln Ala Gly Lys Pro Val Thr Leu
625                 630                 635                 640
Asp Thr Gly Phe Tyr Asp Arg Ala Lys Met Gly Ile Gly Thr Thr Phe
            645                 650                 655
Ala Gly Pro Val Val Ile Glu Gln Tyr Asp Ser Thr Thr Val Ile Pro
            660                 665                 670
Pro Gly Phe Thr Gly Thr Val Asp Asp Ala Gly Asn Leu Val Ile Ala
        675                 680                 685
Cys Pro Ala Val Thr Gln Thr Val Glu Lys Leu Ala Thr Pro Ile Leu
    690                 695                 700
Met Arg Val Ile Gly Gly Ala Leu Asn Ser Ala Ala Lys Glu Met Ala
705                 710                 715                 720
Ser Val Leu Phe Arg Met Ser Tyr Ser Ser Ile Ile Arg Glu Ser Glu
            725                 730                 735
Asp Leu Gly Ala Gly Leu Phe Asp Lys Asp Gly Asn Val Leu Ala Glu
            740                 745                 750
Ser Asp Ser Thr Pro Met Phe Met Gly Ser Met Pro Lys Ile Val Lys
        755                 760                 765
Gly Val Ile Ser Val Leu Gly Asp Asp Ile His Asp Gly Asp Val Ile
    770                 775                 780
Leu His Asn Asp Pro Tyr Leu Gly Ala Thr His Ser Pro Asp Val Ala
785                 790                 795                 800
Ile Ile Glu Pro Ile Phe His Asp Gly Glu Leu Val Gly Phe Ala Gly
            805                 810                 815
Ala Ser Gly Gln Leu Ile Asp Asn Gly Gly Ala Phe Ser Gly Leu Met
            820                 825                 830
Val Asp Ile Gln Asp Val Gln Ser Glu Gly Thr Ile Phe Arg Ala Val
        835                 840                 845
```

| | | | | | | | | | | | | | | |
|---|---|---|---|---|---|---|---|---|---|---|---|---|---|---|
| Lys | Val | Tyr | Glu | Lys | Gly | Val | Arg | Gln | Glu | Ser | Leu | Ile | Arg | His | Ile |
| | 850 | | | | 855 | | | | | 860 | | | | | |
| Leu | Asn | Asn | Thr | Arg | Thr | Pro | Thr | Ser | Asn | Glu | Gly | Asp | Phe | Gln | Ala |
| 865 | | | | | 870 | | | | | 875 | | | | | 880 |
| Met | Ile | Ala | Ala | Cys | Asp | Leu | Ala | Lys | Ser | Arg | Tyr | Leu | Ala | Leu | Val |
| | | | | 885 | | | | | 890 | | | | | 895 | |
| Glu | Arg | Tyr | Gly | Arg | Asp | Ser | Val | Arg | Asp | Ala | Gly | Gln | Phe | Trp | Ile |
| | | | 900 | | | | | 905 | | | | | 910 | | |
| Asp | Tyr | Ser | Glu | Arg | Ile | Val | Arg | Gln | Glu | Ile | Ala | Lys | Ile | Pro | Asp |
| | | 915 | | | | | 920 | | | | | 925 | | | |
| Gly | Val | Tyr | Glu | Thr | Glu | Thr | Gly | Tyr | Leu | Asp | Asp | Asp | Gly | Arg | Asn |
| | 930 | | | | | 935 | | | | | 940 | | | | |
| Tyr | Gly | Lys | Lys | Leu | Pro | Ile | Val | Val | Lys | Val | Ile | Val | Glu | Gly | Asp |
| 945 | | | | | 950 | | | | | 955 | | | | | 960 |
| Glu | Ile | Thr | Tyr | Asp | Leu | Thr | Gly | Ser | Ser | Ala | Gln | Val | Pro | Thr | Ala |
| | | | | 965 | | | | | 970 | | | | | 975 | |
| Tyr | Asn | Cys | Ala | Phe | Glu | Gly | Thr | Thr | Val | Ser | Ala | Phe | Thr | Phe | Ile |
| | | | 980 | | | | | 985 | | | | | 990 | | |
| Thr | Arg | Met | Met | Phe | Leu | Asp | Glu | Val | Ala | Phe | Pro | Val | Phe | Val | Pro |
| | | 995 | | | | | 1000 | | | | | 1005 | | | |
| Gln | Asn | Glu | Gly | Met | Leu | Lys | Ala | Leu | Lys | Val | Ile | Ala | Pro | Lys | Gly |
| | 1010 | | | | | 1015 | | | | | 1020 | | | | |
| Thr | Ile | Phe | Asn | Pro | Asn | Tyr | Pro | Ala | Ala | Thr | Phe | Ser | Arg | Phe | Ser |
| 1025 | | | | | 1030 | | | | | 1035 | | | | | 1040 |
| Gln | Val | Gln | Arg | Ala | Val | Asp | Leu | Ala | Leu | Arg | Ala | Leu | Ala | Pro | Val |
| | | | | 1045 | | | | | 1050 | | | | | 1055 | |
| Met | Pro | Glu | Arg | Val | Thr | Ala | Gly | Asn | Ser | Ala | His | Ile | His | Phe | Met |
| | | | 1060 | | | | | 1065 | | | | | 1070 | | |
| Ser | Tyr | Ser | Gly | Trp | Asp | Glu | Lys | Gln | Gly | Glu | Tyr | Trp | Val | Tyr | Leu |
| | | 1075 | | | | | 1080 | | | | | 1085 | | | |
| Glu | Val | Asn | Glu | Gly | Ser | Tyr | Gly | Ala | Arg | Gln | Asp | Ser | Asp | Gly | Pro |
| | 1090 | | | | | 1095 | | | | | 1100 | | | | |
| Asp | Ser | Val | Asp | Asn | Leu | Ile | Ala | Asn | Thr | Arg | Asn | Asn | Pro | Ile | Glu |
| 1105 | | | | | 1110 | | | | | 1115 | | | | | 1120 |
| Glu | Leu | Glu | Trp | Arg | Phe | Pro | Met | Arg | Thr | Asp | Arg | Tyr | Glu | Leu | Arg |
| | | | | 1125 | | | | | 1130 | | | | | 1135 | |
| Glu | Asp | Pro | Ala | Ala | Ala | Gly | Glu | Tyr | Arg | Gly | Gly | Ile | Gly | Ile | Val |
| | | | 1140 | | | | | 1145 | | | | | 1150 | | |
| Arg | Glu | Asn | Thr | Phe | Leu | Glu | Asp | Thr | Ala | Val | Thr | Cys | Glu | Gly | Glu |
| | | | 1155 | | | | | 1160 | | | | | 1165 | | |
| Arg | His | Asp | Ser | Asp | Val | Pro | Trp | Gly | Ala | Tyr | Gly | Gly | His | Asp | Gly |
| | 1170 | | | | | 1175 | | | | | 1180 | | | | |
| Leu | Asn | Ala | Ser | Leu | Ile | Lys | Asn | Pro | Gly | Arg | Asp | Gly | Glu | Glu | Ser |
| 1185 | | | | | 1190 | | | | | 1195 | | | | | 1200 |
| Trp | Pro | Ser | Lys | Val | Thr | Gly | Arg | Gln | Leu | Gln | Ala | Gly | Asp | Ser | Leu |
| | | | | 1205 | | | | | 1210 | | | | | 1215 | |
| Gln | Ile | Thr | Val | Pro | Ser | Gly | Gly | Gly | Phe | Gly | Asp | Pro | Leu | Lys | Arg |
| | | | 1220 | | | | | 1225 | | | | | 1230 | | |
| Asn | Pro | Leu | Gln | Val | Leu | Glu | Asp | Val | Leu | Asp | Gly | Phe | Thr | Thr | Thr |
| | | | 1235 | | | | | 1240 | | | | | 1245 | | |
| Glu | Ala | Ala | Ser | Arg | Asp | Tyr | Gly | Val | Ile | Leu | Lys | Thr | Val | Asn | Gly |
| | | | | 1250 | | | | | 1255 | | | | | 1260 | |
| Gln | Leu | Thr | Val | Asp | Leu | Ala | Ala | Thr | Ala | Val | Lys | Arg | Glu | Asn | Ala |
| 1265 | | | | | 1270 | | | | | 1275 | | | | | 1280 |

Val Ser Glu Leu Ser His Thr Asn
                1285

( 2 ) INFORMATION FOR SEQ ID NO:3:

( i ) SEQUENCE CHARACTERISTICS:
       ( A ) LENGTH: 17 amino acids
       ( B ) TYPE: amino acid
       ( D ) TOPOLOGY: linear ( x i ) SEQUENCE DESCRIPTION: SEQ ID NO:3:

Met Lys Arg Ile Gly Val Asp Val Gly Gly Thr Phe Thr Asp Leu Tyr
   1            5                   10                  15
   Phe ( 2 ) INFORMATION FOR SEQ ID NO:4:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:4:

ATGAARMGRA THGGNGT                                                                              17

( 2 ) INFORMATION FOR SEQ ID NO:5:

( i ) SEQUENCE CHARACTERISTICS:
       ( A ) LENGTH: 17 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:5:

ATGAARMGYA THGGNGT                                                                              17

( 2 ) INFORMATION FOR SEQ ID NO:6:

( i ) SEQUENCE CHARACTERISTICS:
       ( A ) LENGTH: 50 base pairs
       ( B ) TYPE: nucleic acid
       ( C ) STRANDEDNESS: single
       ( D ) TOPOLOGY: linear ( x i ) SEQUENCE DESCRIPTION: SEQ ID NO:6:

ATGAAGCGCA TCGGCGTGGA CGTGGGCGGC ACGTTCACCG ATCTGTACTT                                          50